(12) United States Patent
Antakly et al.

(10) Patent No.: US 6,683,050 B1
(45) Date of Patent: Jan. 27, 2004

(54) COMPOUNDS WITH ANTI-KS AND ANTI-HIV ACTIVITY

(75) Inventors: Tony Antakly, Montreal (CA); Ram M. Sairam, Dollard-des-Ormeaux (CA)

(73) Assignee: Altachem Pharma Ltd., Edmonton (CA)

( * ) Notice: Subject to any disclaimer, the term of this patent is extended or adjusted under 35 U.S.C. 154(b) by 0 days.

(21) Appl. No.: 09/494,500

(22) Filed: Jan. 31, 2000

Related U.S. Application Data

(63) Continuation of application No. PCT/CA98/00731, filed on Jul. 30, 1998.
(60) Provisional application No. 60/054,543, filed on Aug. 1, 1997, now abandoned.

(51) Int. Cl.[7] .............................................. A01N 37/18
(52) U.S. Cl. ................................ 514/2; 514/8; 514/21; 530/326; 530/834
(58) Field of Search .................. 514/2, 8, 21; 530/326, 530/834

(56) References Cited

U.S. PATENT DOCUMENTS 5,677,275 A * 10/1997 Lunardi-Iskandar et al. ... 514/8
5,851,997 A * 12/1998 Harris ......................... 514/21

OTHER PUBLICATIONS

Gill et al. "The effects of preparations of human chrorionic gonadotropin on AIDS–related Kaposi's sarcoma", New England Journal of Medicine, vol. 335, No. 17(Oct. 24, 1996), pp. 1261–1269. R11.N4.*

* cited by examiner

*Primary Examiner*—Jeffrey Stucker
(74) *Attorney, Agent, or Firm*—Paul S. Sharpe

(57) ABSTRACT

The present invention relates to a compound having anti-KS and anti-HIV pharmaceutical activity which comprises an HCG-like inhibitory protein and fragments or derivatives thereof, said protein and fragments thereof are isolated from a biologically active fraction of APL-HCG, wherein said protein has a molecular weight of about 3,500 or of about 13,000 Dalton, and wherein said protein and fragments thereof are adsorbed polypropylene plastic supports. A pharmaceutical composition for the prevention and/or treatment of Kaposi's sarcoma (KS) and HIV which comprises an therapeutically effective amount of at least one compound of the present invention in association with a pharmaceutically acceptable carrier. A method for the prevention, treatment and/or reduction of Kaposi's sarcoma and HIV expression in AIDS patients, which consists in administering the composition to the patient.

4 Claims, 10 Drawing Sheets

FIG_4

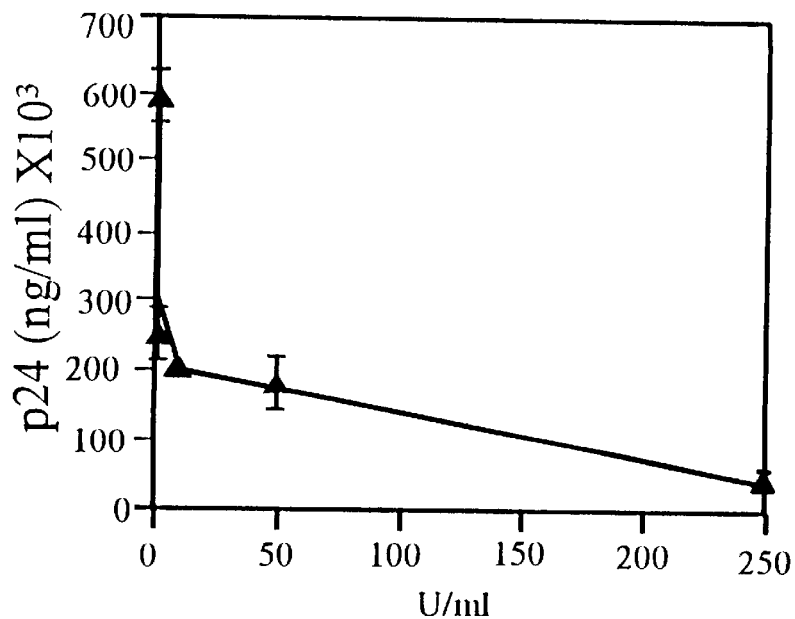
A. HIP Fraction
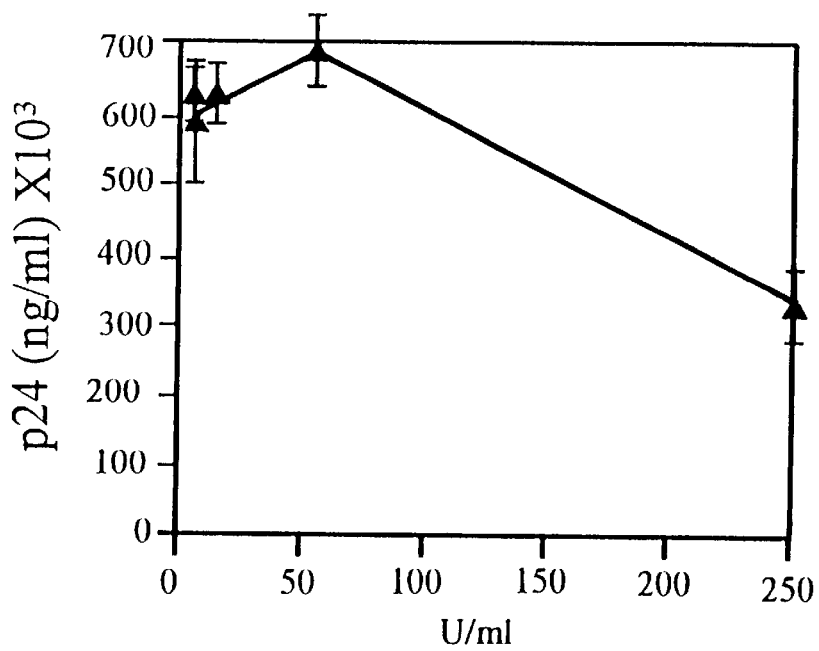
B. Recombinant hCG
FIG. 9

SEQUENCE LISTING

```
<160> NUMBER OF SEQ ID NOS:  4

<210> SEQ ID NO 1
<211> LENGTH: 20
<212> TYPE: PRT
<213> ORGANISM: Artificial Sequence
<220> FEATURE:
<223> OTHER INFORMATION: anti-KS and anti-HIV compound

<400> SEQUENCE: 1

Ser Lys Glu Pro Leu Arg Pro Arg Cys Arg Pro Ile Asn Ala Thr Leu
```

```
-continued 1               5                   10                  15
Ala Val Glu Lys
            20

<210> SEQ ID NO 2
<211> LENGTH: 13
<212> TYPE: PRT
<213> ORGANISM: Artificial Sequence
<220> FEATURE:
<223> OTHER INFORMATION: anti-KS and anti-HIV compound

<400> SEQUENCE: 2

Ala Pro Asp Val Gln Asp Lys Phe Thr Arg Gln Ile Met
1               5                   10

<210> SEQ ID NO 3
<211> LENGTH: 15
<212> TYPE: PRT
<213> ORGANISM: Artificial Sequence
<220> FEATURE:
<223> OTHER INFORMATION: anti-KS and anti-HIV compound
<223> OTHER INFORMATION: Xaa at positions 12, 14, and 15 are
      unknown amino acid residues

<400> SEQUENCE: 3

Ala Pro Asp Val Gln Asp Lys Phe Thr Arg Gln Xaa Met Xaa Xaa
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: anti-KS and anti-HIV compound
<223> OTHER INFORMATION: Xaa at position 9 is an unknown
      amino acid residue

<400> SEQUENCE: 4

Ser Lys Glu Pro Leu Arg Pro Arg Xaa Arg Pro Ile Asn Ala Thr Leu
1               5                   10                  15

Ala Val Glu Lys
            20
```

US 6,683,050 B1

COMPOUNDS WITH ANTI-KS AND ANTI-HIV ACTIVITY

This application is a continuation of PCT/CA98/00731 filed Jul. 30, 1998 designating the United States and claiming priority of U.S. Provisional Patent Application Ser. No. 60/054,543 filed Aug. 1, 1997 (now abandoned).

BACKGROUND OF THE INVENTION (a) Field of the Invention

The invention relates to compounds which exhibit anti-KS and anti-HIV activity, pharmaceutical compositions and method of treatment thereof.

(b) Description of Prior Art

Kaposi's sarcoma (KS) is the most common tumour in AIDS subjects which afflicts high mortality (Friedman-Kien A E et al., 1990, *J Am Acad Dermatol* 22:1237–1250). Less aggressive forms can also occur in non-AIDS subjects of the Mediterranean area and equatorial Africa as well as in renal transplant patients following treatment with immunosuppressive drugs (Friedman-Kien A E et al., 1990, *J Am Acad Dermatol* 22:1237–1250). The pathogenesis and therapy of KS remain enigmatic (Bais C. et al., 1998, *Nature* 391:86). For unknown reasons, occurrence of KS is higher in males than in females. For example, in the West, approximately 95% of AIDS-KS subjects are men. Although, hormonal dependence of KS has been demonstrated in the case of glucocorticoid and retinoid (Guo W X et al., 1996, *Am J Pathol* 148: 1999–2008; Guo W X et al., 1995, *Am J Pathol* 146: 727–734; Guo W X et al., 1995, *Cancer Res* 55: 823–829), sex steroids do not seem to be directly involved in KS pathogenesis. Recently, Lunardi-Iskandar et al. (Lunardi-Iskandar Y et al., 1995, *Nature* 375: 64–68) reported that the placental hormone human chorionic gonadotropin (HCG), displays anti-KS activity and prevents tumours in immunodeficient mice. This preliminary finding could otentially have significant therapeutic impact as demonstrated in clinical trials (Gill PS et al., 1996, *New Engl J Med* 335: 1261–1310; Gill P S et al., 1997, *J. Natl. Cancer Inst.* 89: 1797) and may shed light on basic understanding of this disease particularly regarding the sexual dimorphism issue. Though the role of HCG is principally to sustain pregnancy, it is becoming increasingly apparent that this hormone, possibly along with other active molecules, may be responsible for numerous other phenomena. The low transmission rate of HIV across the placenta (Prober C G et al., 1991, *Ped Infect Dis J* 10: 684–695) as well as the low incidence of Kaposi Sarcoma in women including those previously infected with the virus has led to the suspicion that pregnancy and/or reproductive hormones (such as related LH, see Lunardi-Iskandar Y et al., 1995, *Nature* 377: 21–22) may be involved in curtailing the propagation of the virus. Studies by Bourinbaiar (Bourinbaiar AS et al., 1995, *Immunol Lett* 44: 13–18) indicate that the hormone HCG or its β subunit may have an anti-HIV effect. The action of HCG on gonadal cells is mediated by a G-protein coupled trans-membrane receptor which interacts with the dimeric hormone (α and β complex) with very high affinity and specificity (review Segaloff D L et al., 1993, *Endocr Rev* 14: 324–347). In such a system, it is very well known that either one of the individual α and β subunits have extremely low reactivity towards the membrane bound receptor (Pierce J G et al., 1981, *Ann Rev Biochem* 50: 465–495; Sairam M R, 1983, *In: Hormonal Proteins and Peptides*. Li C. H., ed., pages 1–79) but complete activity can be regained by appropriate (1:1) recombination of the two subunits. Lunardi-Iskandar's and Bourinbaiar's data (Lunardi-Iskandar Y et al., 1995, *Nature* 375: 64–68; Bourinbaiar A S et al., 1995, *Immunol Lett* 44: 13–18) suggest the involvement of an "unconventional" mode of action for HCG in KS. In fact, they reported a biological activity for the β HCG, a notion which contradicts the generally accepted paradigm that the dimeric form of the hormone is required for triggering hormonal responses in classical target tissues. While stirring a controversy (Lunardi-Iskandar Y et al., 1995, *Nature* 377: 21–22; Berger P et al., 1995, *Nature* 377: 21; Rabkin C S et al., 1995, *Nature* 377: 21–22; Krown S E, 1996, *New Engl J Med* 335: 1309–1310), these findings raise intriguing and potentially novel issues.

There is reported in Nature Medicine (Vol. 4, No. 7, July 1998) that the anti-KS activity of crude hCG preparations is still a mystery.

It would be highly desirable to be provided with compounds which would exhibit anti-KS and anti-HIV activity.

SUMMARY OF THE INVENTION

One aim of the present invention is to provide with compounds which would exhibit anti-KS and anti-HIV activity.

In accordance with one preferred embodiment of the present invention there is provided a compound having anti-KS and anti-HIV pharmaceutical activity which comprises an RCG-like inhibitory protein and fragments thereof, the protein and fragments thereof are isolated from a biologically active fraction of APL™-HCG ("APL™" is the commercial trade name of the clinical-grade HCG sold by Wyeth-Ayerst), wherein said protein has a molecular weight of about 3,500 or of about 13,000 Dalton, and wherein said protein and fragments thereof are adsorbed to polypropylene plastic supports, such as tubes or pipette tips among others.

A preferred polypropylene plastic tube includes those sold by Sarstedt (Numbreht, Germany) cat #57.512 and cat #68.752.

In accordance with another preferred embodiment of the present invention there is provided purified protein and derivatives and fragments thereof having anti-KS and anti-HIV pharmaceutical activity which is a HCG-like inhibitory protein and derivatives and fragments thereof which are adsorbed to polypropylene plastic supports, and wherein said protein has an amino acid sequence selected from the group consisting of:

Ser-Lys-Glu-Pro-Leu-Arg-Pro-Arg-Glu-Arg-Pro-Ile-Asn*-Ala-Thr-Leu-Ala-Val-Glu-Lys SEQ ID NO:1; and Ala-Pro-Asp-Val-Gln-Asp-Lys-Phe-Thr-Arg-Gln-Ile-Met-Ala-Thr SEQ ID NO:2.

The purified protein of the present invention is referred to as HIP or HCG-like Inhibitory Protein.

In other embodiments, the derivatives contain one or more D-amino acids or non-natural amino acids.

In accordance with another preferred embodiment of the present invention there, is provided a pharmaceutical composition for the prevention and/or treatment of Kaposi's sarcoma (KS) and/or HIV which comprises a therapeutically effective amount of at least one compound of the present invention in association with a pharmaceutically acceptable carrier.

In accordance with another preferred embodiment of the present invention there is provided a pharmaceutical composition for the prevention and/or treatment of Kaposi's sarcoma (KS) and/or HIV which comprises a therapeutically effective amount of at least one protein of the present invention in association with a pharmaceutically acceptable carrier.

In other embodiments, the pharmaceutical composition is formulated as a controlled release formulation.

In accordance with another preferred embodiment of the present invention there is provided a pharmaceutical composition for the prevention and/or treatment of Kaposils sarcoma (KS) and/or HIV which comprises a therapeutically effective amount of a derivative of a protein having anti-KS and anti-HIV pharmaceutical activity which is a HCG-like inhibitory protein which is adsorbed to polypropylene plastic supports, and wherein said protein has an amino acid sequence selected from the group consisting of:

Ser-Lys-Glu-Pro-Leu-Arg-Pro-Arg-Glu-Arg-Pro-Ile-Asn*-Ala-Thr-Leu-Ala-Val-Glu-Lys SEQ ID NO:1; and Ala-Pro-Asp-Val-Gln-Asp-Lys-Phe-Thr-Arg-Gln-Ile-Met-Ala-Thr SEQ ID NO:2 in association with a pharmaceutically acceptable carrier.

In accordance with another preferred embodiment of the present invention there is provided a method for the prevention, treatment and/or reduction of Kaposi's sarcoma and/or HIV expression in AIDS patients, which comprises administering to said patient a therapeutically effective amount of a compound of the present invention.

In accordance with another preferred embodiment of the present invention there is provided a method for the prevention, treatment and/or reduction of Kaposi's sarcoma and/or HIV expression in AIDS patients, which comprises administering to said patient a therapeutically effective amount of a protein of the present invention.

In accordance with another preferred embodiment of the present invention there is provided a method for the prevention, treatment and/or reduction of Kaposi's sarcoma and/or HIV expression in AIDS patients, which comprises administering to said patient a therapeutically effective amount of a pharmaceutical composition of the present invention.

In accordance with another preferred embodiment of the present invention there is provided a method to purify the compound or protein of the present invention, which comprises the steps of:

a) subjecting a biologically active fraction of APL-HCG or urinary extract containing said compound or protein to a polypropylene plastic support for a time sufficient for adsorption of said compound or protein to occur; and b) washing the support and releasing the adsorbed compound or protein therefrom.

In accordance with another preferred embodiment of the present invention there is provided a method of evaluating inhibitory activity of anti-KS and anti-HIV compound, which comprises by measuring AP1 gene activity.

In other embodiments, measuring of said AP1 gene activity is effected by measuring binding to DNA response element.

For the purpose of the present invention the following terms are defined below.

"HIP": HCG-like Inhibitory Protein;

"HPLC": high-pressure liquid chromatography; and

"APL": commercial trade name of the clinical-grade HCG sold by Wyeth-Ayerst, cat. #DIN 02168936.

The expression "derivatives and fragments thereof" is intended to mean any derivatives and fragments of the protein of the present invention which exhibit anti-KS and anti-HIV pharmaceutical activity effective for the prevention, treatment and/or reduction of Kaposi's sarcoma in AIDS patients. The derivatives may include one or more D-amino acids or non-natural amino acids. The derivatives and fragments are functional and substantially exhibit the biological activity of the protein of the present invention.

BRIEF DESCRIPTION OF THE DRAWINGS

FIG. 9 illustrates the effect of HIP on HIV expression; and

DETAILED DESCRIPTION OF THE INVENTION

Figure 1:
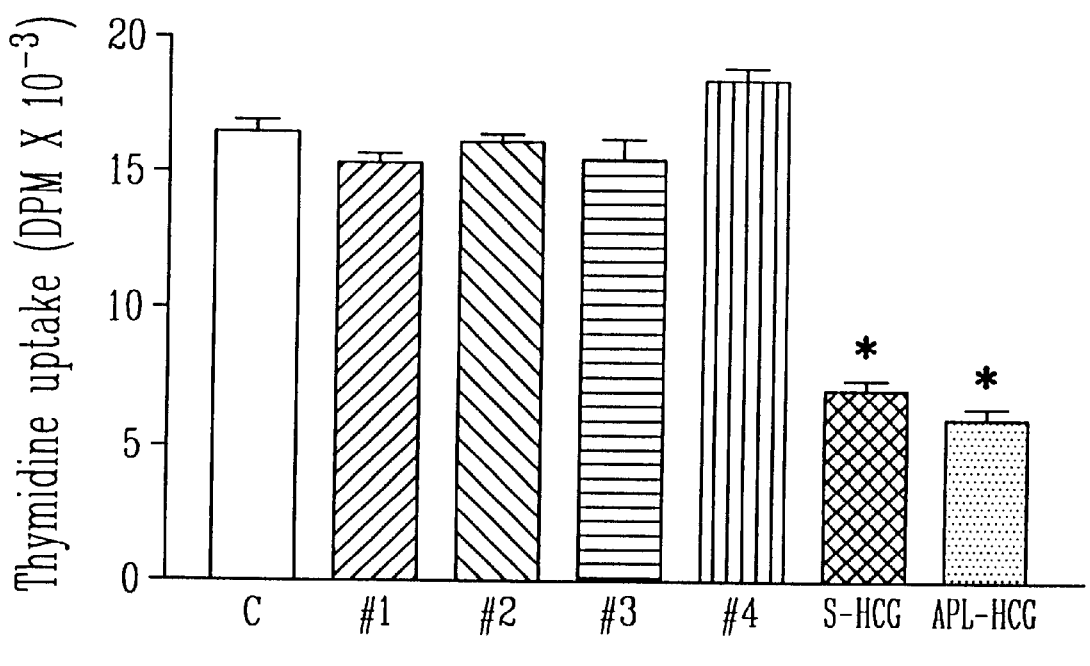
FIG. 1 illustrates the effect of HCG from different commercial sources on KS-Y1 cell proliferation.

Kaposi's sarcoma (KS), a sexually dimorphic disease inflicting high mortality in AIDS, remains at present without effective treatment. A recent report (Lunardi-Iskandar Y et al., 1995, Nature 375: 64–68) showed that the placental glycoprotein hormone, human chorionic gonadotropin (HCG), and surprisingly its β subunit, inhibit tumorigenicity and metastasis of Kaposi's sarcoma cells in mice xenografts. The anti-KS efficacy of a commercial HCG was subsequently demonstrated in clinical trials (Gill P S et al., 1996, New Engl J Med 335: 1261–1310; Gill P S et al., 1997, J. Natl. Cancer Inst. 89: 1797). In addition, earlier studies by Bourinbaiar (Bourinbaiar, A. S. et al., 1992, FEBS. Lett. 309: 82–84; Bourinbaiar A S et al., 1995, Immunol Lett 44: 13–18) and by Gallo's group (Lunardi-Iskandar Y et al., 1998, Nature Medicine 4:428–434) indicate that the β subunit of HCG (or peptides derived thereof) have anti-HIV effects.

The Applicants have been working for several years on the cellular and molecular aspects of KS regulation by hormones. Recent studies in the Applicants' laboratory confirm that commercial HCG preparations (known to be about 25% pure) display significant inhibitory action in a dose-dependent manner. However, pure and biologically active HCG has no effect on Kaposi's sarcoma growth in culture suggesting that a contaminant (or degradation product) may be the active agent.

The Applicants have subfractionated commercial HCG preparations based on molecular size and each fraction was tested with respect to inhibition of KS cell growth, HCG radioreceptor binding and steroidogenic bioactivity. The Applicants' results demonstrate that the anti-KS activity resides among low molecular weight components, and not in bona fide (macromolecular) HCG. Interestingly, the Applicants have identified a transcription factor which may be the target for regulation by the anti-KS components. The Applicants have concluded that, as yet unidentified molecules, present in the commercial HCG preparations, are responsible for the growth inhibitory effects wrongfully attributed to HCG.

Surprisingly, and in accordance with the present invention, there is provided the identification of a purified HIP protein having anti-KS and anti-HIV pharmaceutical activity. This protein is an HCG-like inhibitory protein and is adsorbed to polypropylene plastic supports, and has an amino acid sequence selected from the group consisting of:

Ser-Lys-Glu-Pro-Leu-Arg-Pro-Arg-Glu-Arg-Pro-Ile-Asn*-Ala-Thr-Leu-Ala-Val-Glu-Lys SEQ ID NO:1; and Ala-Pro-Asp-Val-Gln-Asp-Lys-Phe-Thr-Arg-Gln-Ile-Met-Ala-Thr SEQ ID NO:2.

Sources of HCG

Two commercial HCG samples were tested. The first one, under the trade name of APL, was provided by Wyeth-Ayerst, Montreal (Lot #C84662A was generously donated and cat. #DIN-02168936 was purchased), it should be emphasized that APL was used in the earlier studies (Lunardi-Iskandar Y et al., 1995, Nature 375: 64–68; Gill P S et al., 1996, New Engl J Med 335: 1261–1310). Two samples were also purchased from Sigma, St-Louis, Mo. (lot #26H 1040). Pure HCG dimer as well as α-HCG and β-HCG were obtained from NIDDK (Bethesda, Md.). Recombinant HCG was obtained from Organon, Oss, the Netherlands. All HCG samples, previously stored lyophilised, were dissolved in PBS and frozen as aliquots.

Assessment of Cell Proliferation

The KS-Y1 (Lunardi-Iskandar Y et al., 1995, Nature 375: 64–68) was isolated from an HIV-patient while the subline designated N-1506 (Lunardi-Iskandar Y et al., 1995, Nature 375: 64–68) of the original KS-SLK cell line originated from an immunosupressed subject (Herndier B G et al., 1994, AIDS 8: 575–581). These cell lines were provided by Dr. Lunardi-Iskandar (N. I. H., Bethesda) . The KS cells were passaged and the culture medium was changed every other day in presence or in absence of any of the HCG samples mentioned above for the indicated periods ranging from 24–96 hrs. $^3$H-thymidine incorporation was measured as described (Guo W X et al., 1996, Am J Pathol 148: 1999–2008; Guo W X et al., 1995, Am J Pathol 146: 727–734) In most experiments, data are reported as means±SEM of quadruplet determinations. Statistical analysis was determined by student t-test.

Fractionation of APL on SEPHADEX™ G-100

Three vials of APL (10 000 IU/vial) were pooled for fractionation by dissolving in 1.5 ml of 0.05 M $NH_4 HCO_3$. The clear solution was loaded on a column of SEPHADEX™ G-100 ("SEPHADEX™" G-100" are beads for gel filtration preparation prepared by cross linking dextran with epichlorohydrin, available from Pharmacia, Baie d'Urfé, Qc) (1.5×90 cm) equilibrated in the same solvent. Fractions of 1.7 ml were collected and pooled into seven fractions (see FIG. 3). A small portion of each was saved for estimating HCG equivalent activity and the remainder was lyophilized.

HCG Receptor Binding Activity

A convenient test for HCG, a hormone which efficiently binds to the LH receptor, is to perform radioreceptor assays using membrane preparations of adult pig testes as described in detail (Sairam M R, 1983, In: Hormonal Proteins and Peptides. Li C. H., ed., pages 1–79; Manjunath P et al., 1982, J Biol Chem 257: 7109–7115). Standard (CR-125 HCG from NICHD, Bethesda) or test samples were tested for $^{125}$I-HCG binding as described (Sairam M R, 1983, In: Hormonal Proteins and Peptides. Li C. H., ed., pages 1–79). The total binding activity in each of the seven fractions was calculated and expressed as, ug HCG equivalent per fraction.

Steroidogenic Activity

HCG is a highly potent steroidogenic hormone, therefore one reliable bioassay consists of incubating mouse Leydig tumour cells (MA-10, originally obtained from Dr. M. Ascoli, Iowa) with the test material as described (Sairam M R, 1983, In: Hormonal Proteins and Peptides. Li C. H., ed., pages 1–79). Progesterone in the medium was estimated by radioimmunoassay (Sairam M R, 1983, In: Hormonal Proteins and Peptides. Li C. H., ed., pages 1–79).

Electrophoretic Mobility Gel Shift Assay (EMSA)

Nuclear extracts were prepared from KSY-1 cell cultures according to the original procedure of Smeal (Smeal T et al., 1989,. Genes Develop. 3:2091–2100). Binding reactions for AP-1 sites (TRE, TPA Response Element) were carried out as described (Smeal T et al., 1989,. Genes Develop. 3:2091–2100, and reviewed in Saatcioglu F et al., 1994, Semin. Cancer Biol. 5:347–359). Synthetic collagenase TRE oligonucleotide probe of the sequence 5'-GGATCCGATGAGTCAGCCA-3' (SEQ ID NO:5) was end labelled with $^{32}$P-ATP and EMSA performed as described (Sineal T et al., 1989,. Genes Develop. 3:2091–2100). Specificity was ascertained by using. 100 molar excess of unlabelled TRE. The signal was quantified by phosphorimager analysis using the software by Molecular Dynamics (Sunnyvale, Calif.).

Pure HCG Has no Inhibitory Activity in KS Cells (FIG. 1)

Initial experiments were designed to confirm the inhibitory action of HCG. The effects on the two different KS cell lines were compared. In cells pre-treated with a commercial HCG preparation (Sigma or APL) an inhibitory effect was elicited ($p<0.05$) in all KS cell lines. In preliminary experiments a dose-dependent inhibition of cell growth was noted.

The two commercial HCG products (APL and Sigma) were tested, and near identical inhibition was obtained (FIG. 1), right-hand two bars). However, some HCG shipments were more potent than others.

Samples were used at an equivalent concentration of 50 U/ml (FIG. 1). Note that upon treatment with Sigma-HCG (S) or Ayerst-HCG (APL), KS cell growth was significantly reduced as compared with the vehicle-treated cells (C). In contrast, no inhibitory effect was noted using preparations of highly purified HCG. Legend: 1=dimeric HCG; 2=α HCG; 3=β HCG; 4=unrelated human urinary protein pool; *$p<0.05$.

Next, the anti-KS activity of a well characterized, pure dimeric HCG, pure α or β subunits and recombinant HCG was verified. Neither one of these pure HCG's inhibited KS growth (FIG. 1, #1–3). The biological activity of these compounds was examined by induction of steroidogenesis in cultured Leydig cells. As expected, either recombinant or pure HCG elicited the classic biological responses, while neither α nor β HCG displayed any steroidogenic action.

Figure 2:
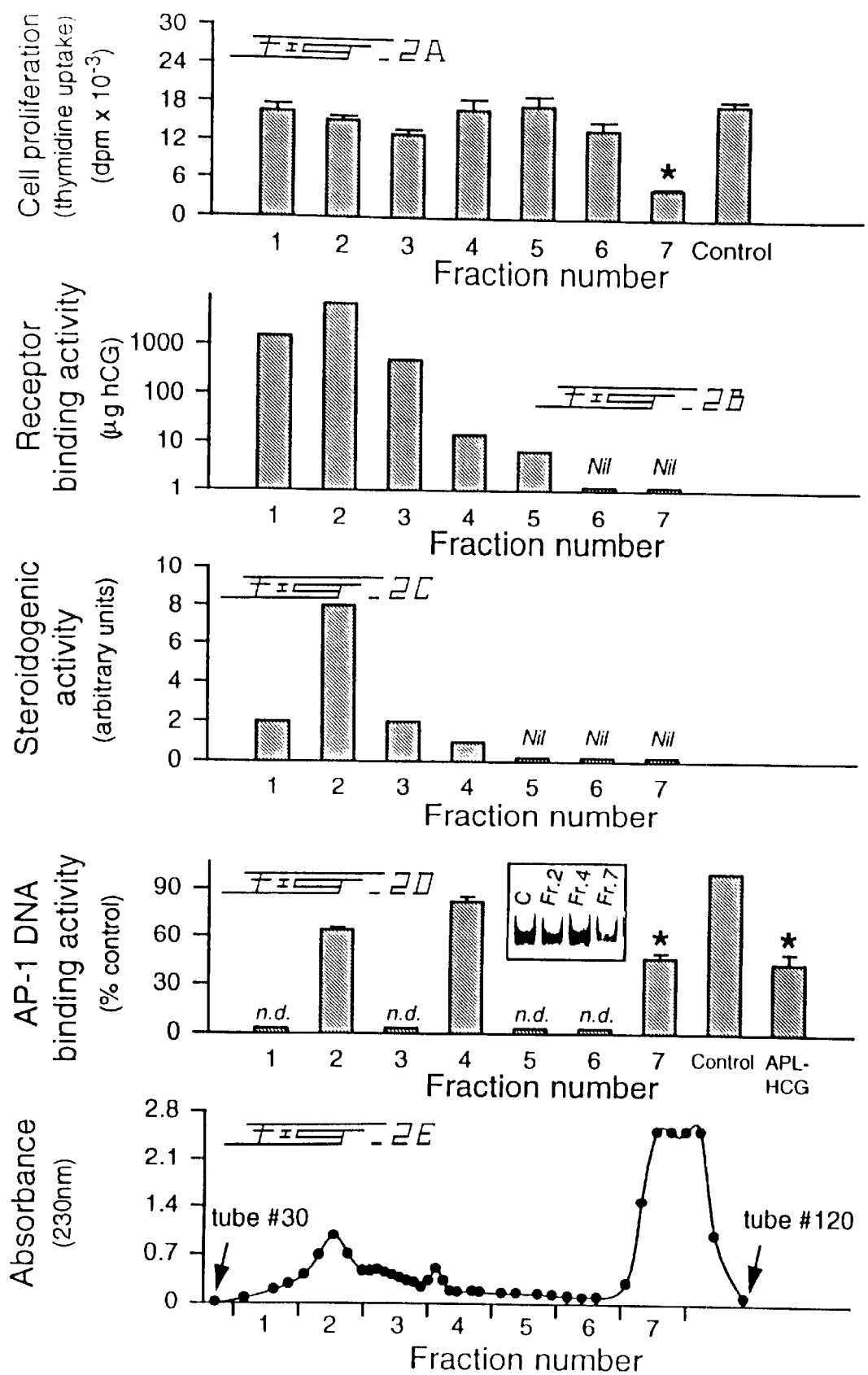
FIG. 2 illustrates the fractionation and activity profile of APL-HCG.

Molecular Sieving of Crude HCG (FIG. 2)

Generally, the pregnancy hormone ampouled into vials for clinical use is only about 25% pure for HCG as evaluated by biological activity and biochemical analyses (Manjunath P et al., 1982, *J Biol Chem* 257: 7109–7115). The commercial HCG (APL) was sorted into 7 distinct fractions using SEPHADEX™ chromatography (FIG. 2).

The contents of 3 vials of clinical grade APL (10,000 IU each) were dissolved in 0.05 M $NH_4 HCO_3$ and subjected to molecular sieving on a column of SEPHADEX™ G-100 (1.5×90 cm). The eluted protein/peptide fractions monitored at A230 nm (panel E) were separated into seven pools identified as fraction pools #1–7 on the X-axis. A total of 120 tubes (1.75 ml/tube) were collected. Lyophilized material in each pool was reconstituted in KS culture medium (without serum), and evaluated for cell proliferation (panel A). HCG receptor binding in pig testicular membranes (panel B) and steroidogenic activity in MA-10 cells (panel C) were determined. Panel D: bar graphs show quantitative densitometric scanning of AP-1 binding and insert shows the actual EMSA protein-DNA complexes of fractions (fr) 2,4 and 7; nd=not determined. KSY-1 cells were treated with the indicated reagents at an equivalent concentration 100 U/ml for 4 days. Note clear segregation of HCG hormone activity on gonadal cells (pool 2) and inhibitory action on KS cells (pool 7) *p<0.05.

Over 85% HCG receptor binding activity (FIG. 2B) was recovered in the first two pooled fractions where high molecular weight proteins of the size of pure HCG would emerge. The Ve/Vo ratio of the early major fraction (pool #2) corresponded to bona fide HCG. These fractions may also contain the hormone subunits ($\alpha/\beta$) or their degraded products in addition to other unidentified materials present in the crude extract. Fraction #7 consists, as shown in previous studies (Sairam M R, 1983, *In: Hormonal Proteins and Peptides*. Li C. H., ed., pages 1–79), of relatively small peptides along with other agents present in the APL formulation. Either the steroidogenic or the binding activity that is characteristic of HCG (but not its subunits) was highest in the 2nd fraction (FIGS. 2B and C). These results are consistent with receptor binding assays in which only the dimeric ($\alpha–\beta$ combined) HCG but not the individual subunits or their cleaved products are biologically active (Sairam M R, 1983, *In: Hormonal Proteins and Peptides*. Li C. H., ed., pages 1–79; Manjunath P et al., 1982, *J Biol Chem* 257: 7109–7115). On the contrary, only fraction #7 contained KS inhibitory activity.

Figure 3:
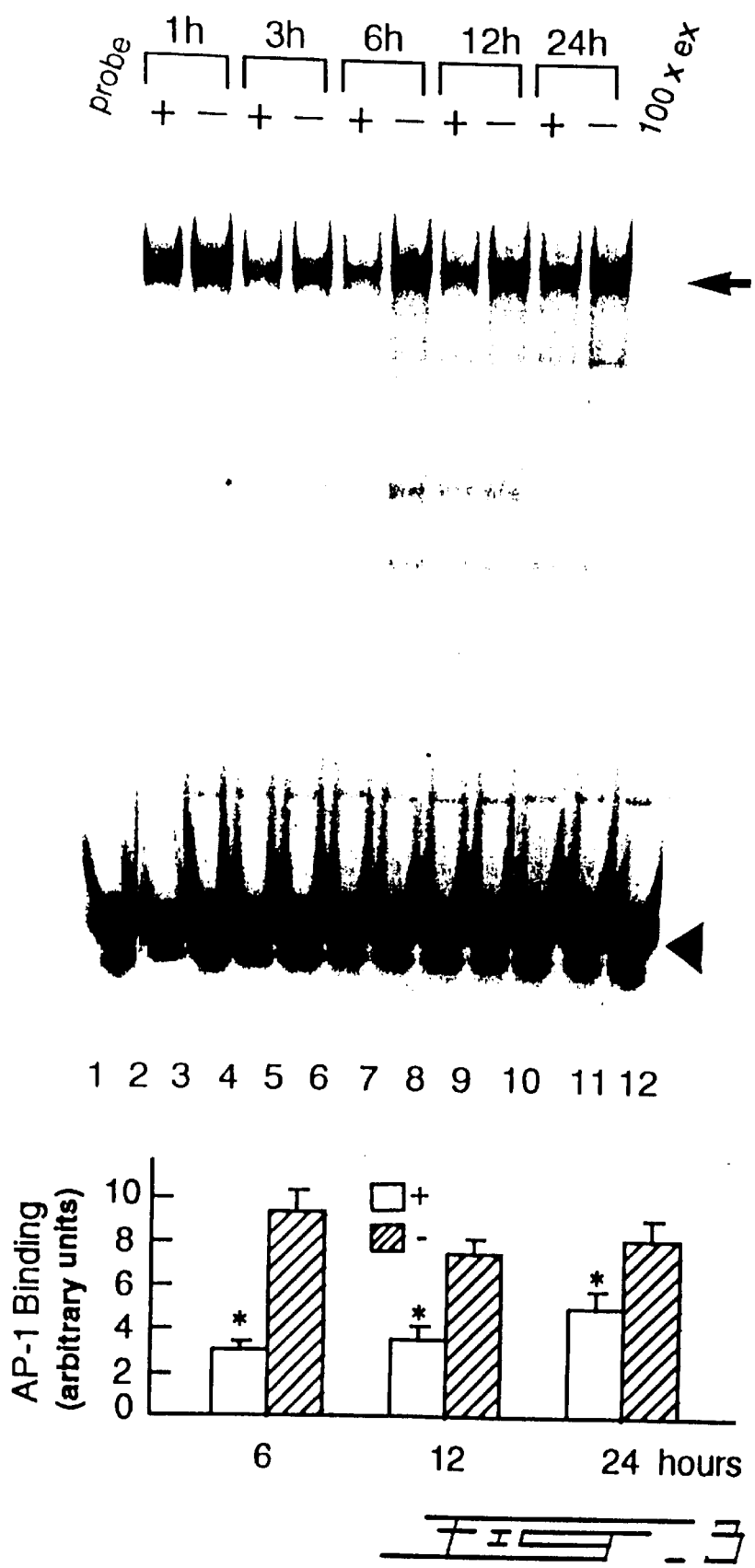
FIG. 3 illustrates the time-course effect of APL-HCG on inhibition of AP-1 binding in KSY-1 cells.

Down-regulation of AP-1 Binding by HCG Components (FIG. 3)

Activating protein-1 (AP-1) is a transcriptional activator which is induced by 12-O-tetradecanyl phorbol-13-acetate (TPA) tumor promoter, several growth factors and various extracellular stimuli (reviewed in Saatcioglu F et al., 1994, *Semin. Cancer Biol.* 5:347–359). AP-1 consists of proteins of jun and fos families which associate to form homo-(jun/jun) or heterodimers (jun/fos) and recognize a consensus sequence 5'-TGA G/C TCA-3' known as TPA Response Element (TRE) present on AP-1 regulated genes. AP-1 complexes are considered to play important roles in several signal transduction pathways such as growth stimulation, differentiation, neuronal excitation and transformation (Saatcioglu F et al., 1994, *Semin. Cancer Biol.* 5:347–359). APL-HCG and components in fraction 7 significantly inhibited AP-1 binding to TRE in KSY-1 cells (FIG. 2D). APL-HCG inhibited AP-1 binding by 1.5, 3 and 2 fold respectively after 3, 6 and 12 hours of treatment (FIG. 3).

Cells were incubated with 50 IU/ml APL-HCG (+) or with vehicle (−) for the indicated time periods (FIG. 3). Nuclear extracts were prepared and EMSA was performed. Results shown are representative of three experiments. Arrow-head points to free probe. 100ex.=100 fold excess unlabelled probe. Top shows the actual gel shifts while bottom panel provides quantitative phosphorimager measurement of the major band (arrow); * denotes p<0.05 as compared to vehicle-treated.

A dose-response was also observed with near maximal effect noted at approximately 100 IU/ml. Therefore, repression of AP-1 may be an important pathway by which inhibition of KSY-1 cells occurs.

Figure 4:
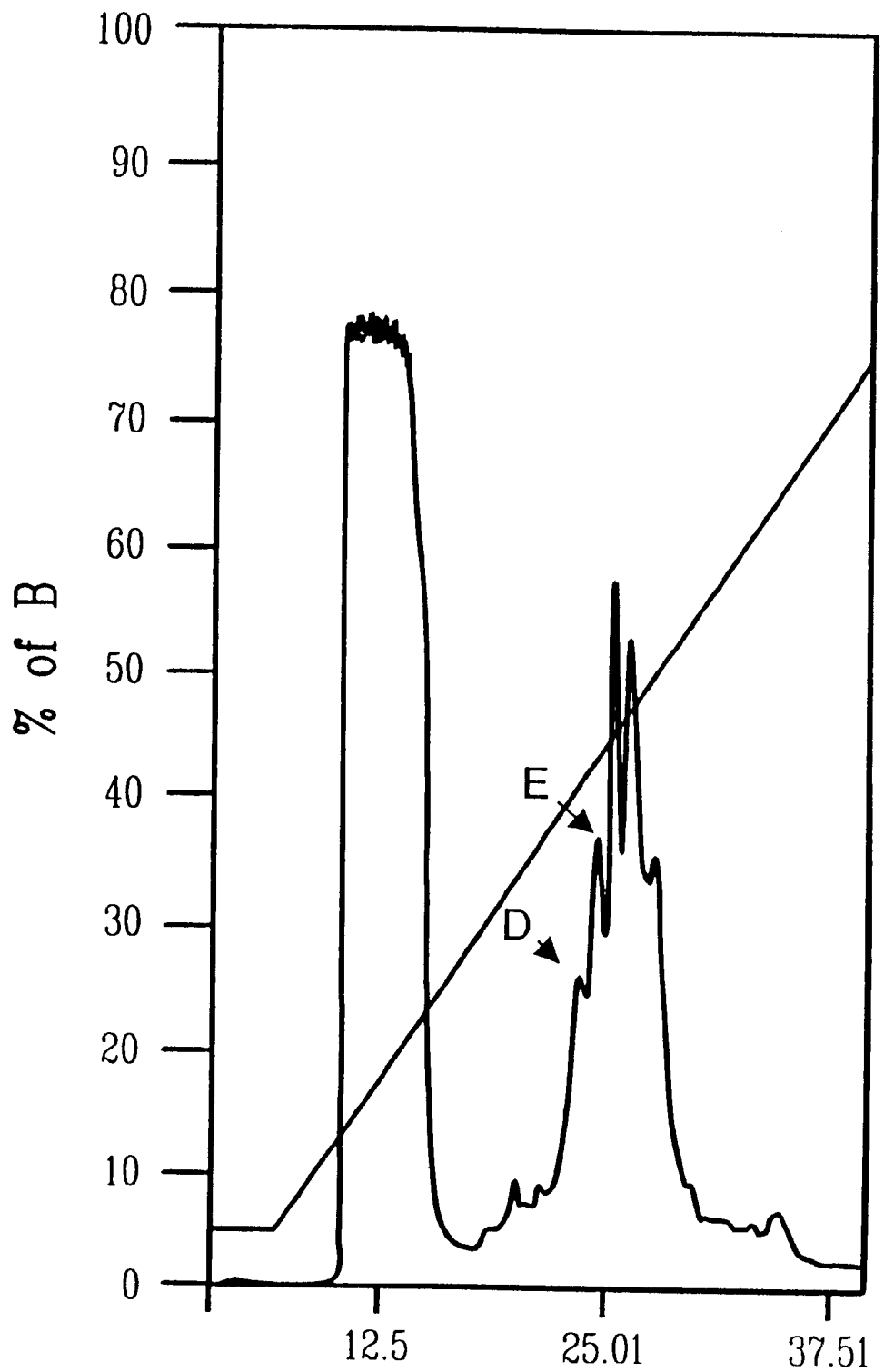
FIG. 4 illustrates the purification of the HIP using reversed phase-HPLC.

Purification of the HIP Using Reversed Phase-HPLC (FIG. 4)

APL was purchased from Wyeth-Ayerst Cat. #DIN 02168936 and shipped in an insulated box packed with refrigerant Upon receipt, APL was stored at 4° C. One APL vial (which contained the dried product) lot #JA(L)3YYF-AB was reconstituted with one (1) ml of the solvent sold with the APL ampoule at room temperature and processed for HPLC within one hour. The powder was readily dissolved resulting in a homogeneous "solution". This "solution" was injected into a Water™ HPLC apparatus fitted with a 7.8×300 mm C-18™ columnn Elution from the column was done using an increasing linear isocratic gradient of acetonitrile in water containing 0.1% trifluoroacetic acid. The gradient was increased from 5% to 75% acetonitrile. The absorbancy was monitored at 220 wavelength during the elation and fractions were collected manually in siliconized polypropylene tubes. When regular (i.e. non-siliconized) tubes were used it was later found that biological activity was lost After collection, the fractions were immediately placed in a Savant™ Speed-vac apparatus in order to dry the samples. The gradient is drawn on FIG. 4; the right-side or Y axis shows the % acetetonile (%B; B: 80% acetonitrile in water containing 0.1% trifluoroacetic acid) and the X axis indicates time, in minutes. The absorbency at 220 nm was recorded and recorded on the Y axis. The two peaks (D & E) indicated by arrows were subsequently found (see FIG. 5 below) to contain the KS inhibitory activity.

Figure 5:
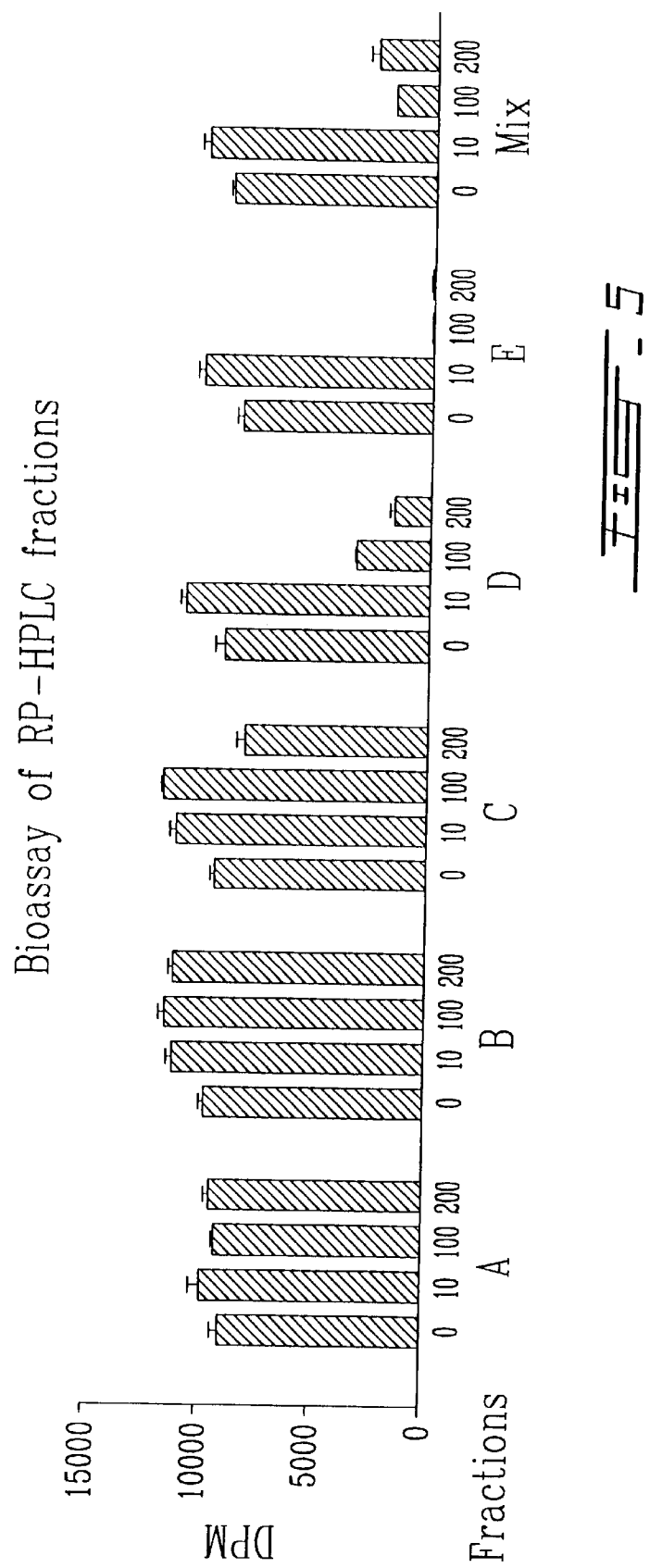
FIG. 5 illustrates the bioassay of the collected fractions following HPLC separation.

Bioassay of the Collected Fractions Following HPLC Separation (FIG. 5)

The fractions (peaks) indicated by arrows on FIG. 4. were lyophilized and each was reconstituted in one (1) ml of RPMI culture medium (without serum) and tested for biological activity using the KS-Y1 cells. Since the original material was supplied as 10 000 IU of HCG, by analogy, it was assumed arbitrarily that one of the fractions should contain arbitrarily 10,000 IU of anti-KS activity. With such an assumption, the doses were evaluated throughout the present application. The biological activity was tested in absence (0) or presence of different doses (10, 100 & 200 IU/ml). The fraction indicated as "mix" represents one pool made by mixing equivalent amounts of fractions A–E. It can be seen from FIG. 5 that fractions D, E and "Mix" display an inhibitory activity.

Figure 6:
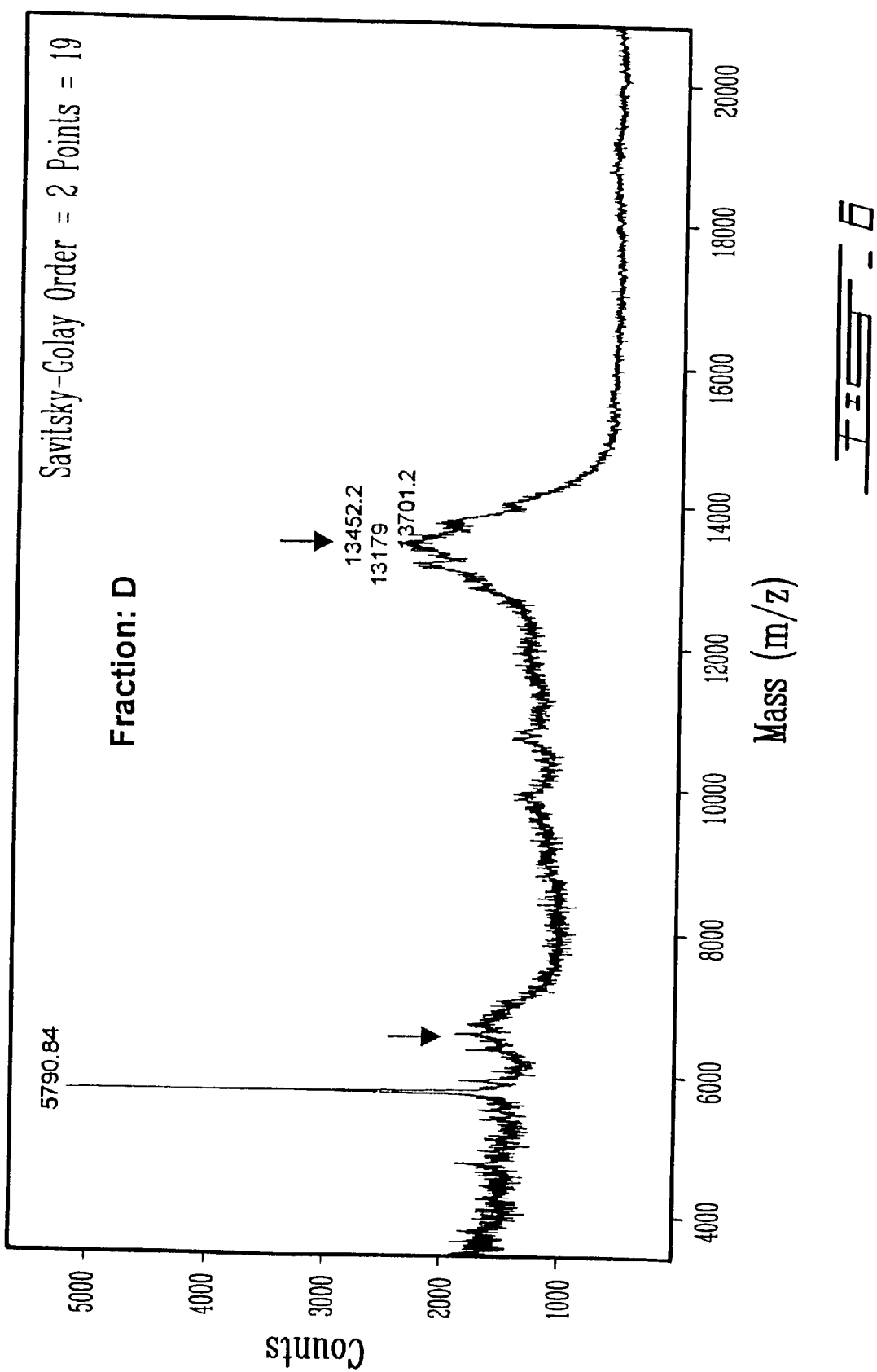
FIG. 6 illustrates the analysis of fraction D by mass spectrometry.
Figure 7:
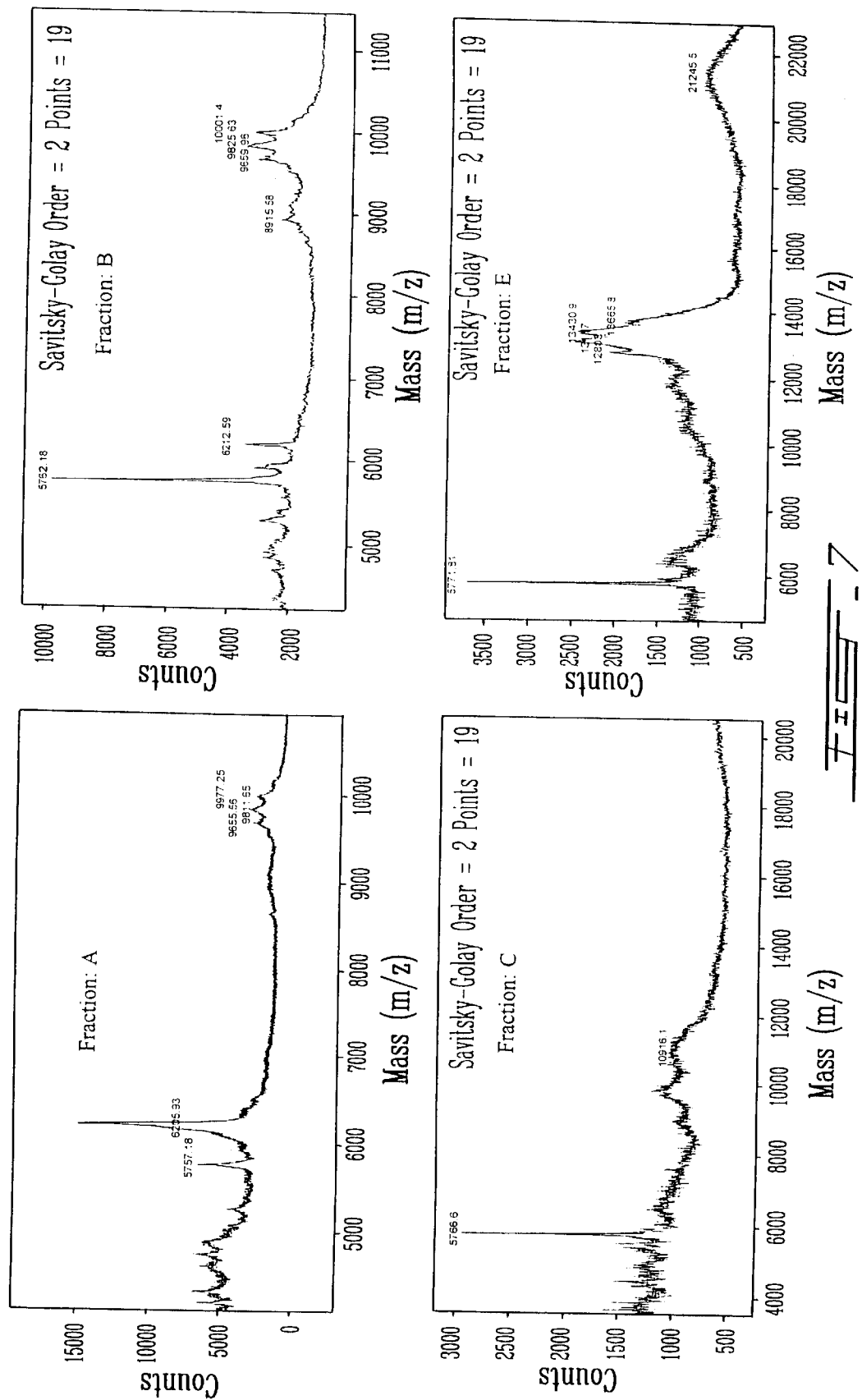
FIG. 7 illustrates the analysis of fraction A+B+C+E by mass spectrometry.
Figure 8:
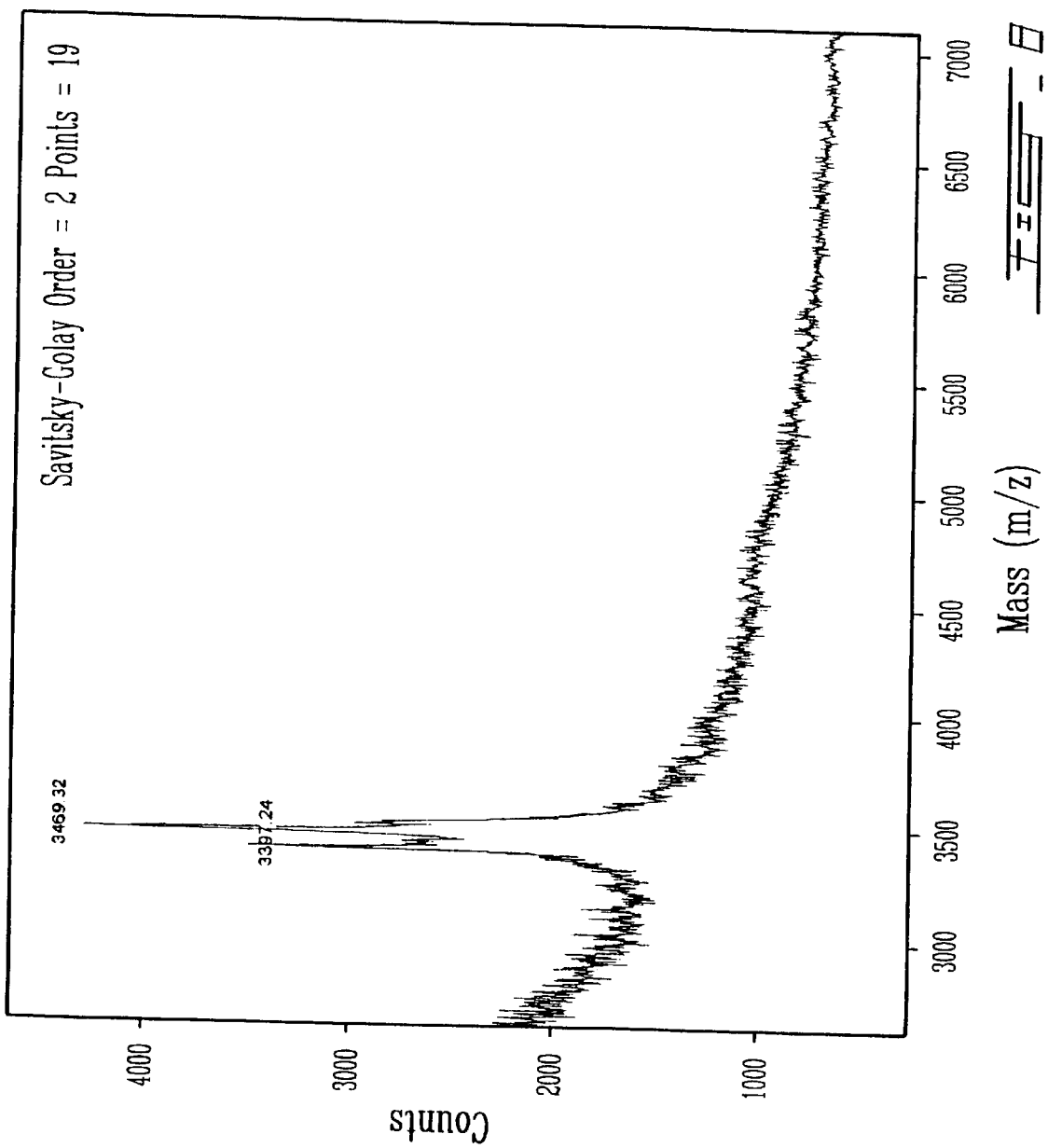
FIG. 8 illustrates the analysis of another low molecular weight fraction by mass spectrometry.

Analysis of the Active Fractions (HIP) by MALDI-TOF Mass Spectrometry (FIGS. 6 and 7)

Briefly, an aliquot of each sample was embedded in a low molecular weight UV-absorbing matrix ($\alpha$-cyano-4-hydroxycinnamic acid) to enhance sample ionization and then subjected to MALDI-TOF (Matrix Assisted Laser Desorption Ionization Time of Flight) mass spectrometry on a Voyager-Delayed Extraction system (Perseptive Biosystem, Framingham, Mass.).

One major peak can be observed containing moieties at approximately 13000 Dalton (FIG. 6). For comparison purposes, the spectrometric analysis of fractions A–C and E are also shown (FIG. 7), note that the 13000 Dalton species is found in both fractions D and E (FIG. 6).

Effect of HIP on HIV Expression (FIG. 9)

The low molecular weight fraction #7 shown earlier to inhibit KS cell proliferation (Kachra et al., 1997, *Endocrinology*, 138:4038–4041), was tested for its anti-HIV activity. Primary cultured human lymphocytes were infected with the virus HIV-IIIB as described (Tremblay et al., 1994, *Embo. J.* 13:774). Immediately following infection, cells were treated with the test material (HCG fractions or recombinant HCG) daily for 10 days at the indicated dose ranging from 1 to 250 IU equivalent. Subsequently, cells were lysed and assayed for the expression of the HIV viral protein p24 as described (Tremblay et al., 1994, *Embo. J.* 13:774). It can be noted that p24 expression is markedly reduced upon treatment with high doses of the fraction containing HIP while recombinant HCG displays no significant affects (FIG. 9).

Figure 10A:
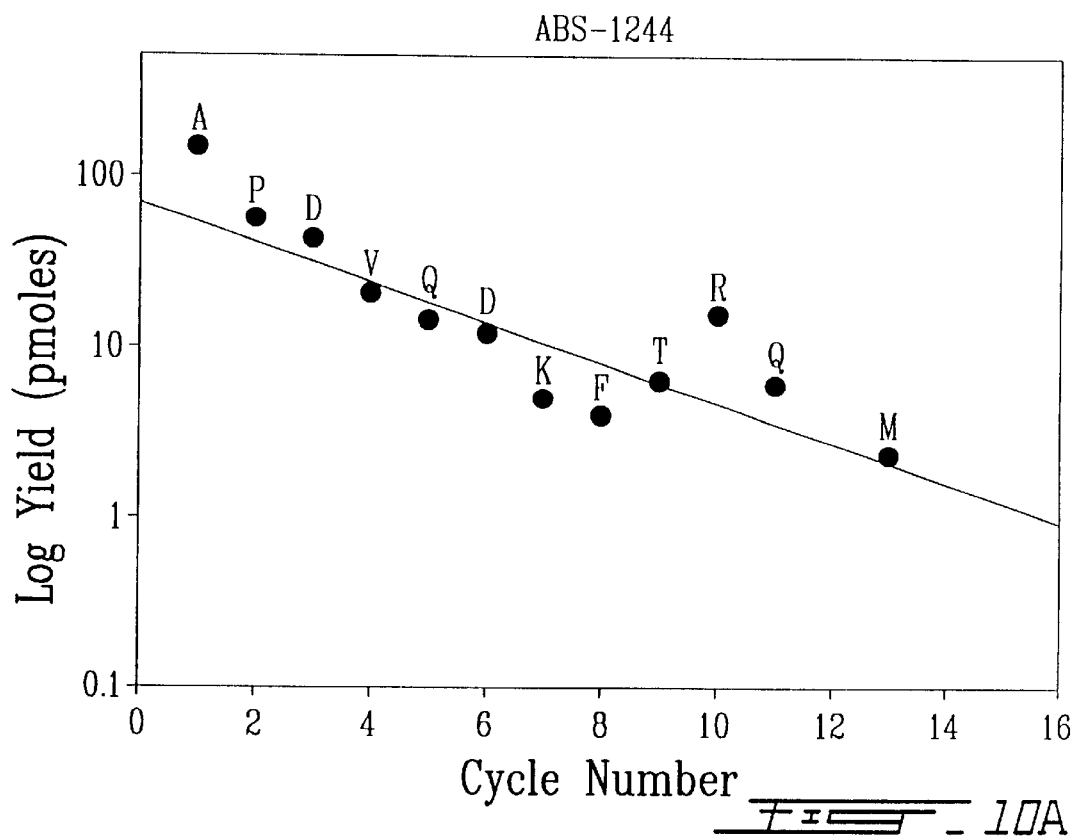
FIGS. 10A and 10B illustrate potential partial sequences of the purified HIP protein of the present invention.
Figure 10B:
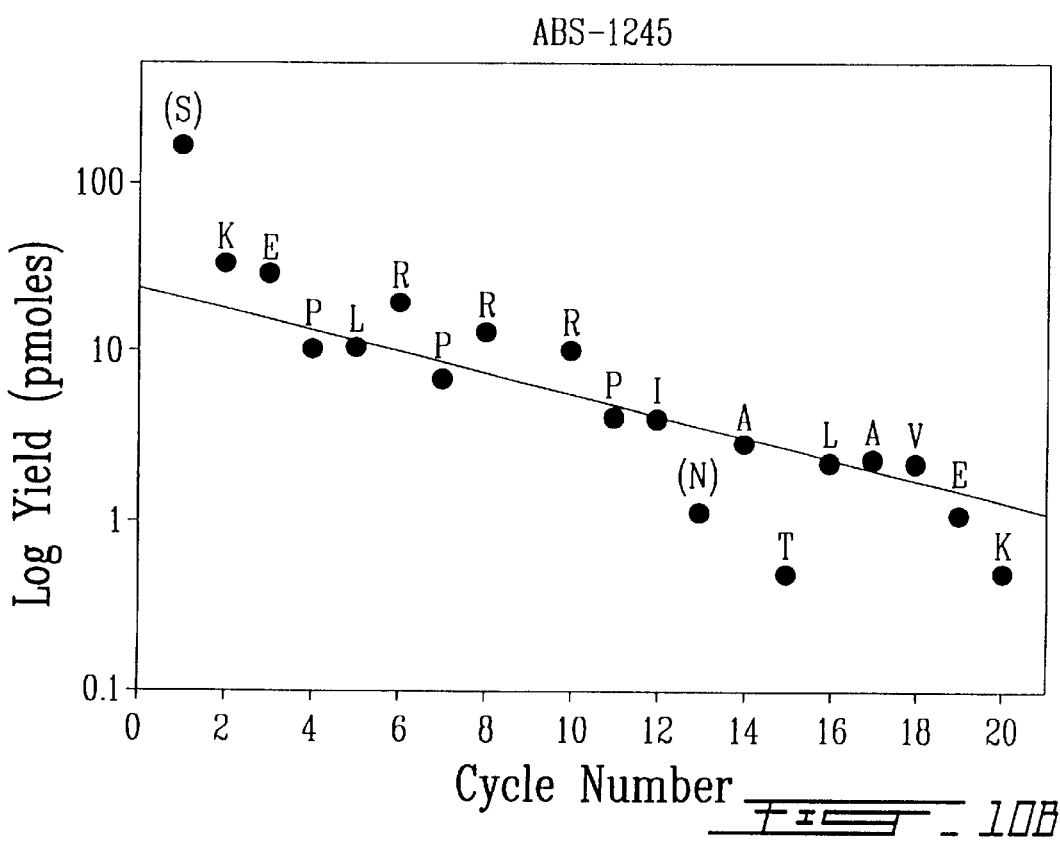

Sequencing of the Proteins Contained in the HIP Fractions (FIGS. 10A and 10B)

Following the HPLC separation, the fractions were tested for biological activity as described above (for FIGS. 4 and 5). Two fractions which contains highest bioactivity were processed for protein sequencing using an automatic sequencing apparatus (Applied Biosystem gas phase sequencer model 470 updated to 475). An internal standard was used consisting of pTH-Nor-Leu. The initial yield efficiency was approximately 50±20 pmoles. After 15 cycle runs, data generated was examined using customary protein analysis. The deduced amino acid sequences were compared with published databases of the GenBank™. It was found that the two sequences contained significant homology with the α- and β-subunits of hCG.

CONCLUSION

The present results provide evidence for the existence of a potentially important compound which inhibits the growth of KS possibly through signalling by the AP-1 pathway. Although the sequencing of the purified active molecule is currently in progress, it is evident that it is neither HCG nor any of its classically unknown subunits.

Judging from its gel permeation chromatographic elution, its size is relatively small and probably less than 10,000–14,000. To obtain further resolution, the technique of HPLC was employed resulting in a separation of protein species into discrete and distinct peaks. Specific individual peaks were found to contain the anti-KS activity. To obtain further data, individual peaks were analyzed by polyacrylamide gel electrophoresis followed by silver staining. In instances where proteins was visualized, a "fuzzy" band was observed, indicating that the proteins comprise closely related species.

At this time, one can only speculate as to whether it is derived from HCG as a cleavage peptide. Indeed, it is known that glycoprotein hormones are metabolized to smaller polypeptides (Sairam M R, 1983, *In: Hormonal Proteins and Peptides*. Li C. H., ed., pages 1–79). The putative cleavage (or related product) could elicit its action via a modified HCG receptor. In fact, the HCG receptor gene is known to be expressed as alternatively spliced variant transcripts (Segaloff D L et al., 1993, *Endocr Rev* 14: 324–347) in a developmentally regulated manner raising the possibility that the putative product could mediate different aspects of hormone action. Such a hypothesis is further strengthened by parallel experiments showing that KS tissues and cell lines express significant levels of HCG receptors whose size and intracellular distribution are different from classical targets cells (Cao H., Sairam M. R. and Antakly T., Abstract #1543, Annual meeting, American Association for Cancer Research, 1996). Alternatively, the active substance could be a degradation product of the β-HCG subunit (such as but not limited to P-core) which is homologous in three-dimensional structure to several growth factors (Lapthorn A J et al., 1994, *Nature* 369: 455–461). Since the initiation and proliferation of KS cells is largely growth factor-dependent, it is possible that β-core fragments act as antagonists for growth factor receptors (reviewed in Guo W X et al., 1996, *Am J Pathol* 148: 1999–2008).

The partial sequences obtained in accordance with the present invention support the view that HIP proteins may be derived from hCG either as: 1) alternate expression of α- or β-subunit; or 2) enzymatic processing of the hCG subunits.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. A pharmaceutical composition having inhibitory activity on Kaposi's sarcoma (KS) and/or HIV which comprises a therapeutically effective amount of at least one compound having anti-KS and/or anti-HIV activity and comprising a sequence selected from the group consisting of SEQ ID NOS: 1 and 4 in association with a pharmaceutically acceptable carrier, wherein said at least one compound is also a polypropylene adsorbing compound which lacks the HCG steroidogenic ability and lacks the ability to bind to the lutropin-choriogonadotropin receptor.

2. A pharmaceutical composition having inhibitory activity on Kaposi's sarcoma (KS) and/or HIV which comprises a therapeutically effective amount of at least one compound having anti-KS and/or anti-HIV activity and comprising SEQ ID NO: 1 in association with a pharmaceutically acceptable carrier, wherein said at least one compound is also a polypropylene adsorbing compound which lacks the HCG steroidogenic ability and lacks the ability to bind to the lutropin-choriogonadotropin receptor.

3. A pharmaceutical composition for the reduction of Kaposi's sarcoma (KS) and/or HIV expression which comprises a therapeutically effective amount of at least one compound having anti-KS and/or anti-HIV activity and comprising a sequence selected from the group consisting of SEQ ID NOS: 1 and 4 in association with a pharmaceutically acceptable carrier, wherein said at least one compound is also a polypropylene adsorbing compound which lacks the HCG steroidogenic ability and lacks the ability to bind to the lutropin-choriogonadotropin receptor.

4. A pharmaceutical composition for the reduction of Kaposi's sarcoma (KS) and/or WV expression which comprises a therapeutically effective amount of at least one compound having anti-KS and/or anti-HIV activity and comprising SEQ ID NO: 1 in association with a pharmaceutically acceptable carrier, wherein said at least one compound is also a polypropylene adsorbing compound which lacks the HCG steroidogenic ability and lacks the ability to bind to the lutropin-choriogonadotropin receptor.

* * * * *